US005409452A

United States Patent [19]

Aversano

[11] Patent Number: 5,409,452

[45] Date of Patent: Apr. 25, 1995

[54] NON-INVASIVE TRACTION DEVICE

[76] Inventor: Louis J. Aversano, 5891 Griscomb Dr., Bensalem, Pa. 19020

[21] Appl. No.: 16,584

[22] Filed: Feb. 10, 1993

[51] Int. Cl.[6] ............ A61F 5/00

[52] U.S. Cl. ............ 602/32; 482/142; 606/241; 606/242

[58] Field of Search ............ 606/237, 240, 241–245; 602/32–36, 38; 482/131, 132, 95, 96, 142, 143, 907; 5/662, 658, 503.1

[56] References Cited

U.S. PATENT DOCUMENTS

| | | | |
|---|---|---|---|
| Re. 32,791 | 11/1988 | Saunders | 602/32 |
| 1,936,363 | 11/1933 | Murray | 606/242 |
| 2,590,670 | 3/1952 | Anderson | 606/243 X |
| 3,548,816 | 12/1970 | Bond | 602/36 |
| 4,144,880 | 3/1979 | Daniels | 606/242 |
| 4,220,147 | 9/1980 | Allen, III | 602/32 X |
| 4,236,265 | 12/1980 | Carradine | 5/658 X |
| 4,951,654 | 8/1990 | Gambale et al. | 606/242 |
| 5,129,881 | 7/1992 | Pope | 602/32 |
| 5,147,287 | 9/1992 | Jewell et al. | 606/242 |

OTHER PUBLICATIONS

Portion of Tru Traction Inc. Brochure.

*Primary Examiner*—Richard J. Apley
*Assistant Examiner*—Linda C. M. Dvorak
*Attorney, Agent, or Firm*—Volpe and Koenig

[57] ABSTRACT

An improved chiropractive table having a seat portion and a back-rest portion. Non-invasive traction devices are attached to the table for applying an upward force and a lateral force to a desired portion of a patient's anatomy. The combined forces produce a stretching force and a rolling moment to provide the desired therapy to the patient.

3 Claims, 3 Drawing Sheets

NON-INVASIVE TRACTION DEVICE

BACKGROUND OF THE INVENTION

1. Field of the Invention

This invention relates to a traction device for applying forces to a portion of a patient's anatomy. More particularly, it relates to a non-invasive means for applying a combination of forces to a desired portion of a patient's anatomy to produce a stretching force and a rolling moment. Most particularly, the present invention finds use in chiropractive tables where a combination of forces are used to align and curve the vertebrae in a patient's neck.

2. Description of the Prior Art

It is known in the chiropractic field to apply forces to a portion of a patient's anatomy in order to adjust the alignment and position of the vertebrae in a patient's spinal cord. This is done to relieve discomfort caused by muscle strain or misalignment of the vertebrae, and/or to provide rehabilitative therapy for an injury.

Chiropractive tables for use in applying these forces are known in the art. One such known device, which includes a seat portion and a back-rest portion, utilizes a harness and a spring tension attachment to apply a force to correct the curve and alignment of a person's neck vertebrae. The known device is designed to apply a force to a patient's forehead and forces the patient's head down and backward.

While this device has proven effective to correct the curve and alignment of the neck vertebrae in some cases, it can also cause discomfort due to the compression of the patient's neck and shoulders. When the corrective force is applied in accordance with the existing device, it creates a stretching or tensile force on the anterior side of the vertebrae and a compressive force on the posterior side. It is the compressive force between the posterior portions of the vertebrae which can cause discomfort in some patients.

SUMMARY OF THE INVENTION

The present invention provides an improved chiropractive table having a seat portion and a back-rest portion. Non-invasive traction devices are attached to the chair for applying an upward force and a lateral force to a desired portion of the patient's anatomy. This combination of forces produces a stretching force and a rolling moment to provide the desired therapy.

When used for correcting the curve and alignment of the vertebrae in a patient's neck, the upward and lateral forces combine to produce a stretching force and rolling moment on the neck vertebrae. The combination of forces eliminates the compressive forces between posterior portions of the neck vertebrae, while correcting the alignment and position of the neck vertebrae.

It is an object of this invention to provide a non-invasive means for applying an upward and a lateral force to a desired portion of a patient's anatomy to produce a stretching force and a rolling moment.

It is an object of this invention to provide an improved chiropractive table with means for applying both an upward force and a lateral force to a desired portion of the patient's anatomy.

It is an object of this invention to provide a means for decreasing or eliminating the compressive force between the vertebrae in a patient's neck while they are receiving neck vertebrae alignment therapy.

It is an object of this invention to provide a means for installing the non-invasive traction device in accordance with this invention onto existing chiropractive tables.

DESCRIPTION OF THE PREFERRED EMBODIMENT

Figure 1:
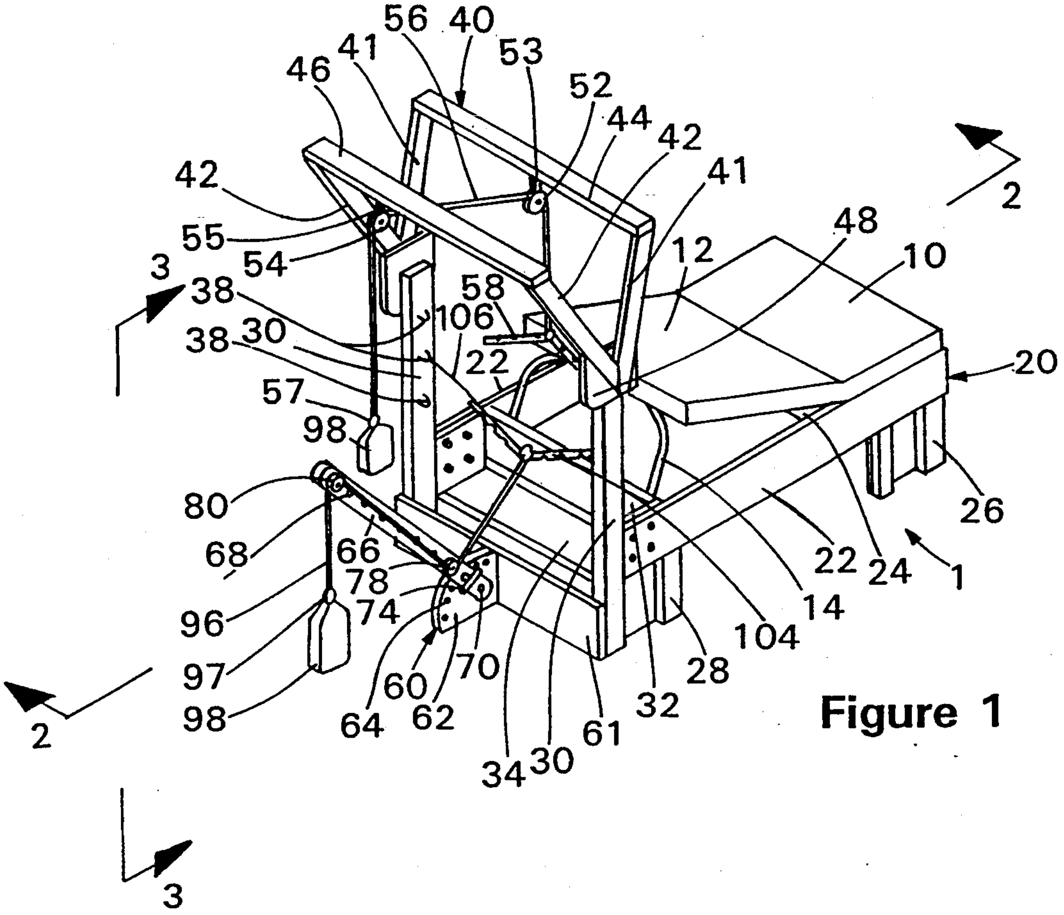
FIG. 1 is a perspective view of the preferred embodiment of the invention.

FIG. 1 shows a perspective view of the preferred embodiment of the chiropractive table 1. The chiropractive table 1 is comprised of a frame 20 to which a seat portion 10 and a hinged back-rest portion 12 are attached. Parallel sides 22 of the frame 20 are connected by a seat support cross-member 24 and a second cross-member 32. The sides 22 are supported by leg assemblies 26 and 28. Posts 30 extend vertically from each leg 28 at the back end of the chiropractive table 1.

Figure 2:
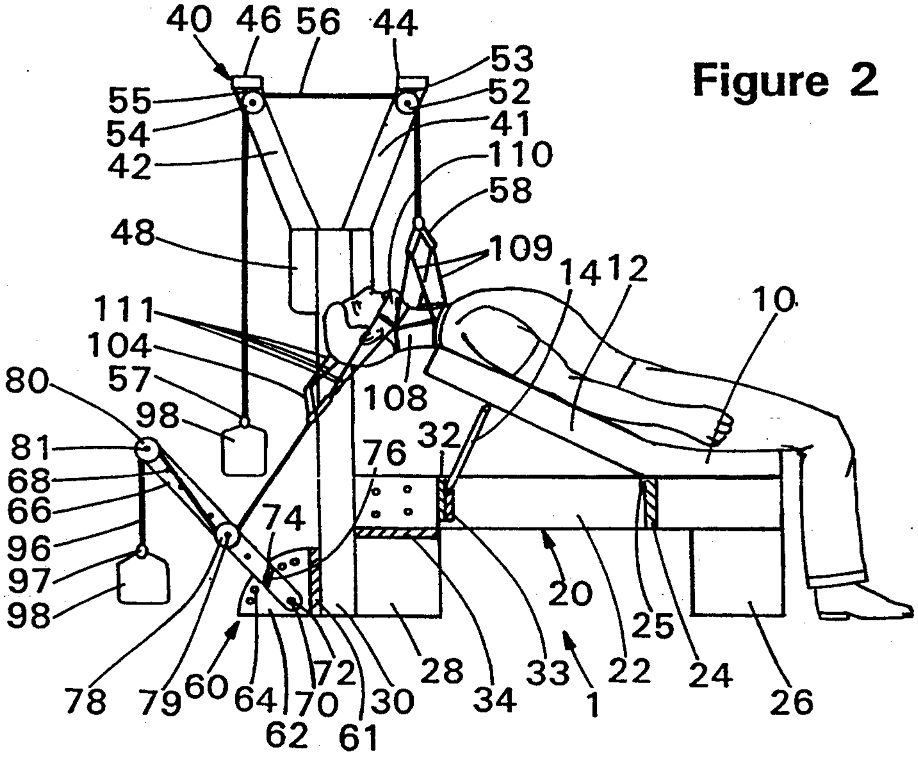
FIG. 2 is a section along line 2—2 in FIG. 1 illustrating the operation of the invention on a patient.

As shown in FIG. 2, the back rest portion 12 is attached to the seat support cross-member 24 by a hinge 25. The back rest portion 12 can be moved from a horizontal position, where it is supported by the sides 22, to an inclined position as shown in FIGS. 1 and 2.

The back rest support 14 is pivotally attached to the back rest portion 12. It is used to support the back rest in the inclined position by engaging the support 14 against a cleat 33 affixed to the second cross-member 32. This will all be known to those skilled in the art.

Figure 3:
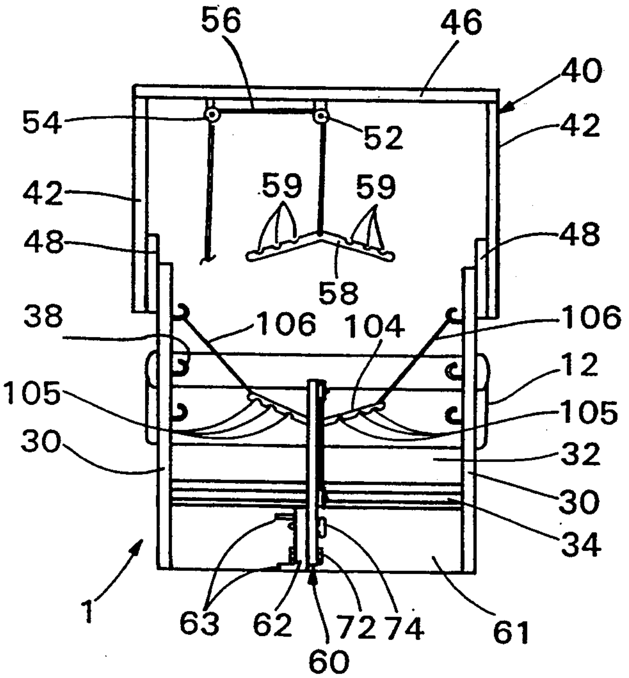
FIG. 3 is a view taken along line 3—3 in FIG. 1.

As shown in FIGS. 1 through 3, a vertical traction device 40 is attached to the vertical supports 30 in a position above the area to be occupied by a patient's head and shoulders. The vertical traction device 40 is comprised of two pairs of aligned frame members 41 and 42 attached to the vertical posts 30 on opposite sides of the table 1. The frame members 41 and 42 on each side of the chair 1 are arranged in a "V"-shaped pattern and are attached to each vertical post 30 by a mounting plate 48. Parallel overhead cross-members 44 and 46 are attached between the respective aligned pairs of frame members 41 and 42. The inner overhead cross-member 44 is located in the space above the area to be occupied by the patient's neck. The outer overhead cross-member 46 is located beyond the area occupied by the table 1.

Pulleys 52 and 54 are attached to the overhead cross-members 44 and 46. The pulley 52 is attached to the inner overhead cross-member 44 at a medial location by a pulley support 53. The second pulley 54 is attached to the outer overhead cross-member 46 in an off center location by pulley support 55. A cord 56 with a hook 57 attached to one end, and a spreader bar 58 attached to its opposite end is threaded through the pulleys 52 and 54. A weight 98 can be suspended from the hook 57. The second pulley 54 is located in an off-center location to provide clearance between the weight 98 and the lateral traction device 60. The vertical traction device 40 provides a means for applying a vertical or upward force to a portion of the patient's anatomy.

An adjustable lateral traction device 60 is attached to the table 1 by a support 61, which is attached between the bases of the vertical posts 30. The lateral traction device 60 is comprised of a sector 62 to which an arm 66 is pivotally attached. The pivotal connection is formed by a pin 70 which is inserted in an aperture 72 which extends through the base of the arm 66 and the sector 62.

The sector 62 contains an array of apertures 64 arranged at a fixed distance from the pivot pin 70. An aperture 76 is located in the base of the arm 66 at an equal distance from the aperture 72. A removable pin 74 is disposed through the aperture 76 and one of the apertures 64 in the array in the sector 62. As will be recognized by those skilled in the art, the angle of the arm 66 can be adjusted and locked into position by removing the pin 74 from the aperture 64, and pivoting the arm 66 about pivot pin 70 such that the aperture 76 is aligned with a desired aperture 64 from the array in sector 62. The pin 74 is then reinserted, locking the arm 66 in the desired position.

Two pulleys 78 and 80 are attached to the arm 66 with pins which are inserted in the arm apertures 68. The arm apertures 68 are arranged in a linear array and are spaced at regular intervals along the arm 66. The upper pulley 80 is attached to the free end of the arm 66. The position of the moveable pulley 78 can be adjusted by removing the pin 79 and repositioning the pulley 78 in alignment with any aperture 68 in the linear array of arm apertures 68 and reinserting the pin 79.

A cord 96 is threaded through the pulleys. The cord 96 has a hook 97 on one end for a weight 98, and has a spreader bar 104 attached to its opposite end. The lateral traction device provides the means for applying a lateral force to a portion of the patient's anatomy. By adjusting the arm 66 and the pulley 78, the angle of application of the lateral force can be varied. The two pulley system also insures adequate clearance between the weight 98 and the floor.

Figure 4:
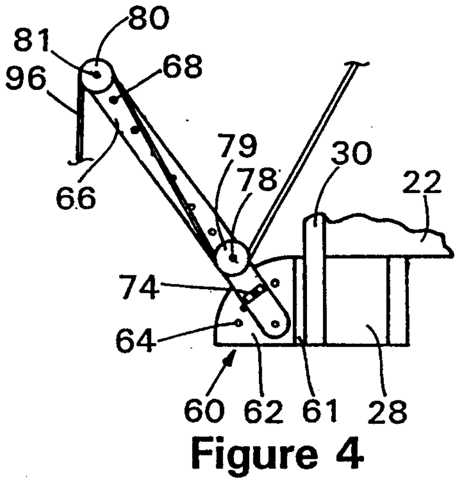
FIG. 4 is and enlarged, partial view of a portion of FIG. 2 showing the lateral traction device.
Figure 5:
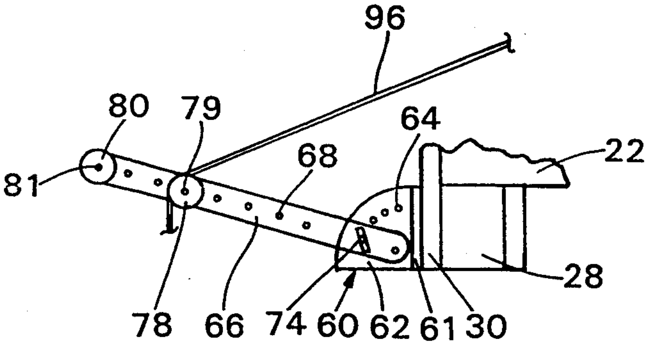
FIG. 5 is a view similar to FIG. 4 showing a second position for the lateral traction device.
Figure 6:
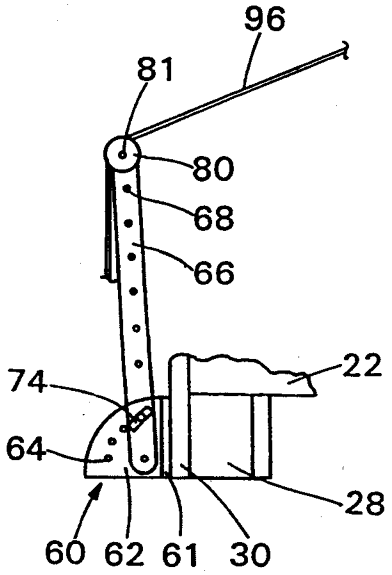
FIG. 6 is a view similar to FIG. 4 showing a third position for the lateral traction device.

As illustrated in FIGS. 4 through 6, the angle of the lateral force can be varied through the adjustment of the arm 66 relative to the sector 62, the movement of the pulley 78 to the various positions along the arm 66, and the path of the cord 96. The configuration shown in FIG. 4 provides for a lateral force in which the downward component is greater than the lateral component. The arm 66 is pinned at a medial location in the array of apertures 64 in the sector 62, and the cord 96 is threaded below the lower pulley 78 and then up and over the upper pulley 80.

The configuration shown in FIG. 5 illustrates the arm 66 in its lowest position, with the pin 74 in the lowest aperture 64 in the array in the sector 62. The cord 96 has been threaded over the lower pulley 78, and the upper pulley 80 is not utilized.

The configuration shown in FIG. 6 illustrates the arm 66 in a near vertical position, with the pin 74 in the uppermost aperture in the array 64 in the sector 62. The cord 96 passes over the upper pulley 80 to provide a lateral force with a minimal downward component.

As illustrated in FIG. 3, both the upper and lower spreader bars 58 and 104 have notches 59 and 105 respectively, for attaching a traction harness. Temporary strings 106 can be attached between the hooks 38, affixed to the posts 30, and the lower spreader bar 104 to temporarily hold it in position while fitting the chin harness 110 on the patient.

As will be recognized by those skilled in the art, the vertical and lateral traction devices 40 and 60 can be fitted onto existing chiropractive tables. The mounting plates 48 can be used to attach the vertical traction device 40, and the support 61 can be used to mount the lateral traction device 60 to the existing posts 30 on existing chiropractive table.

Referring again to FIG. 2, the operation of the chiropractive table 1 will be explained. With the patient seated on the seat portion with the patient's neck extending above the back-rest, the neck harness is placed under the patient's neck and hooked to the upper spreader bar 58. The neck harness attachments 109 are engaged in notches 59 on the spreader bar. A desired weight 98 is attached to the hook 57 on the free end of cord 56. The chin harness 110 is placed about the patient's chin and attached to the lower spreader bar 104 by harness attachments 111 engaged in the notches 105 on the spreader bar. After adjusting the arm 66 to achieve the desired angle of application for the lateral force, a weight 98 is hung from the hook 97 on the free end of cord 96. The two harnesses 108 and 110 apply both an upward and lateral force to the patient's neck vertebrae.

The amount of weight utilized for the upward and lateral forces and the angle at which the lateral force is applied can be adjusted for each patient. By applying the required lateral force to the patient's chin along with the required upward force to the back of the patient's neck, the neck vertebrae can be curved and aligned without any compressive forces acting on or between the neck vertebrae.

Figure 7:
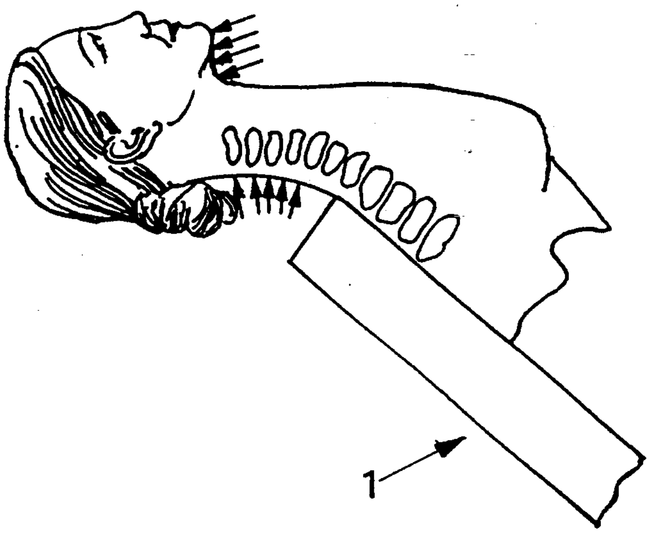
FIG. 7 is a partial view showing the forces applied by the vertical and lateral traction devices and their effect on the patient's neck vertebrae.
Figure 8:
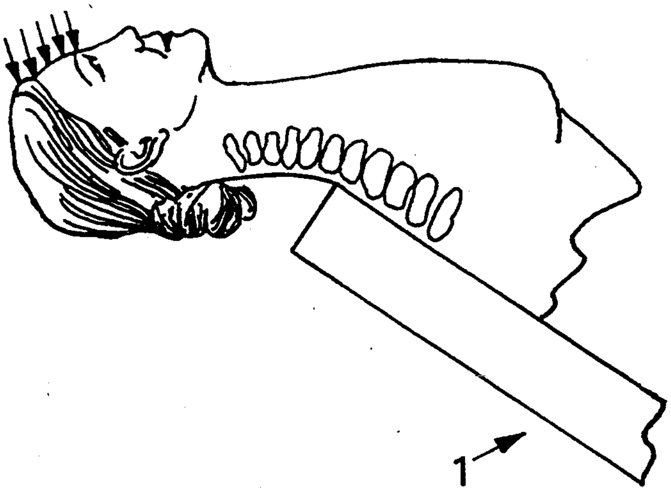
Figure 8 (PRIOR ART)
FIG. 8 is a view similar to FIG. 7 showing the application of force by a prior art device and the effect produced on the patient's neck vertebrae.

FIGS. 7 and 8 show a portion of the patient's anatomy with a representative section through the patient's neck vertebrae. Those skilled in the art will recognize that the neck vertebrae are represented in simplified form for the purpose of this discussion. The arrows in the Figures represent the forces being applied to the patient during therapy.

In FIG. 7, the forces generated by the vertical and lateral traction devices of the present invention are shown. The vertical force acts on the back of the patient's neck, and the lateral force acts on the patient's chin. The resultant combination of these two forces on the patient is a rolling moment and a stretching force which combine to stretch the neck vertebrae apart while achieving proper alignment of the neck vertebrae without applying any compressive forces to the anterior or posterior portions of the neck vertebrae. This effect is illustrated in FIG. 7 where a space exists between the adjacent neck vertebrae which are being uniformly stretched apart.

In contrast, FIG. 8 illustrates the application of force made by the prior art device. The prior art device only applied a single force to the patient's forehead, as illustrated, forcing the patient's head back and down. While this results in a stretching or tensile force on the anterior portion of the patient's neck vertebrae, it also creates a compressive force which acts on the posterior portions of the patient's neck vertebrae. As illustrated, this compressive force on the posterior portion of the neck vertebrae forces these portions into closer contact, which can cause discomfort in some patients.

The present invention can be utilized with a double sling to apply the lateral force to the patient's neck vertebrae. The first sling would be placed under the patient's chin, as shown in FIG. 2, and a second sling (not shown) would be placed under the patient's neck such that it would pull on the back of their head. Both slings would then be attached to the lower spreader bar 104.

The present invention can also be used with shaped neck support pieces attached to the top of the hinged back-rest 12 to assist in curving the patients neck. The neck support pieces can be cylindrical, half cylinders or oblong, and can be loose or attached to the top of the hinged back-rest 12.

While the preferred embodiment has been described with reference to aligning neck vertebrae in a patient, it will be recognized by those skilled in the art that the combination of forces provided can be used on other portions of the patient's anatomy.

I claim:

1. An improved chiropractive table, having a seat portion and a back-rest portion, for use in correcting the curve and alignment of a patient's neck vertebrae by applying a force to a desired portion of the patient's anatomy wherein the improvement comprises:

a non-invasive means for applying an upward force to the patient's neck; and a non-invasive means for applying a lateral force to the patient's neck at a selected angle such that the combination of the upward force and the lateral force reduce compression between the neck vertebrae while correcting their curve and alignment, the non-invasive means for applying the lateral force includes a sector attached to the chiropractive table;

an arm pivotally attached to the sector such that the arm can be pivoted to a number of angular positions relative to the sector;

a means for releasably locking the arm in a given position;

a means for releasably attaching a pulley at a number of locations along the arm; and at least one pulley attached to the arm such that the angular position of the arm and the location of the pulley along the arm determine the angle of the lateral force.

2. The improvement of claim 1 further comprising:

a cord having a spreader bar attached to one end and a means for attaching a weight on the opposite end threaded over the pulley.

3. The improvement of claim 1 further comprising:

two pulleys attached at upper and lower positions along the arm; and a cord having a spreader bar attached to one end and a means for attaching a weight on the opposite end threaded under the lower pulley and over the upper pulley.

* * * * *